United States Patent
Kennedy

(10) Patent No.: US 9,126,816 B2
(45) Date of Patent: Sep. 8, 2015

(54) FLUID SUPPLY SYSTEM

(71) Applicant: Alan John Kennedy, Bellingham, WA (US)

(72) Inventor: Alan John Kennedy, Bellingham, WA (US)

( * ) Notice: Subject to any disclaimer, the term of this patent is extended or adjusted under 35 U.S.C. 154(b) by 0 days.

(21) Appl. No.: 14/209,742

(22) Filed: Mar. 13, 2014

(65) Prior Publication Data

US 2014/0263477 A1 Sep. 18, 2014

Related U.S. Application Data

(60) Provisional application No. 61/778,818, filed on Mar. 13, 2103.

(51) Int. Cl.
| | |
|---|---|
| *B67D 1/00* | (2006.01) |
| *B67D 1/04* | (2006.01) |
| *A61C 1/00* | (2006.01) |
| *A61C 17/02* | (2006.01) |

(52) U.S. Cl.
CPC ............ *B67D 1/0082* (2013.01); *A61C 1/0084* (2013.01); *B67D 1/0412* (2013.01); *A61C 17/0205* (2013.01)

(58) Field of Classification Search
USPC .............. 222/165, 180, 464.1, 518, 511, 512, 222/514, 570, 559, 531, 532, 537, 399, 394, 222/545, 544; 433/80
See application file for complete search history.

(56) References Cited

U.S. PATENT DOCUMENTS

| | | | | |
|---|---|---|---|---|
| 2,046,804 | A * | 7/1936 | Youngblood | 222/192 |
| 2,109,720 | A * | 3/1938 | Deschner | 222/478 |
| 2,159,490 | A * | 5/1939 | Ramsay | 222/83 |
| 2,169,506 | A * | 8/1939 | Simmons | 222/481 |
| 2,178,964 | A * | 11/1939 | Hulse | 222/464.1 |
| 2,182,742 | A * | 12/1939 | Brewer | 222/399 |
| 2,341,950 | A * | 2/1944 | Schepps | 141/387 |
| 2,373,171 | A * | 4/1945 | Daly | 222/309 |
| 2,375,215 | A * | 5/1945 | Davis | 222/394 |
| 3,162,370 | A * | 12/1964 | Moonan et al. | 239/304 |
| 3,191,616 | A * | 6/1965 | Kochner | 137/505.25 |
| 3,702,623 | A * | 11/1972 | Chacko | 137/495 |
| 4,700,872 | A * | 10/1987 | Keyes et al. | 222/162 |
| 4,982,879 | A * | 1/1991 | Corrado et al. | 222/400.7 |
| 5,022,565 | A * | 6/1991 | Sturman et al. | 222/396 |
| 5,329,975 | A * | 7/1994 | Heitel | 141/19 |
| 2003/0077552 | A1* | 4/2003 | Decosterd et al. | 433/84 |
| 2008/0217363 | A1* | 9/2008 | Vitantonio et al. | 222/399 |
| 2012/0282569 | A1* | 11/2012 | Disel | 433/80 |

* cited by examiner

*Primary Examiner* — Donnell Long
(74) *Attorney, Agent, or Firm* — Michael J. Andri

(57) ABSTRACT

A fluid supply system includes a fluid supply subsystem and a fluid bottle subsystem. Pressurized air or other suitable gas supplied to the fluid supply system causes a piston housed within the fluid supply subsystem to translate toward the fluid bottle subsystem, thereby sealing an interface between the fluid supply subsystem and the fluid bottle subsystem. The pressurized air or gas also causes a fluid (e.g., a coolant or rinse liquid) within the fluid bottle subsystem to flow through the piston and out of the fluid supply subsystem where it may be used. The fluid supply system enables the fluid bottle subsystem to be installed or uninstalled from the fluid supply subsystem without requiring bleeding off of the air or gas supplied to the fluid supply system and/or without requiring the fluid bottle subsystem to be rotated or twisted into place relative to the fluid supply subsystem.

20 Claims, 4 Drawing Sheets

FLUID SUPPLY SYSTEM

CROSS REFERENCE TO RELATED APPLICATIONS

This application claims priority to U.S. Provisional Application Ser. No. 61/778,818, titled FLUID SUPPLY SYSTEM, filed Mar. 13, 2013, the entirety of which is hereby incorporated herein by reference.

BACKGROUND

In the field of dentistry, it is accepted practice to rinse a patient's mouth with liquids at intervals and to use liquid coolants for the dental drills or syringes. Example liquids include tap water, distilled water, sterile water, or other suitable rinses and/or coolants. In such case, the liquid is typically contained in a bottle or other container adjacent to the dental chair and supplied with appropriate air pressure to provide a pressurized flow to the dental syringe and drill handpiece operated by the dentist or dental assistant.

SUMMARY

A fluid supply system includes a fluid supply subsystem and a fluid bottle subsystem. Pressurized air or other suitable gas supplied to the fluid supply system causes a piston housed within the fluid supply subsystem to translate toward the fluid bottle subsystem, thereby sealing an interface between the fluid supply subsystem and the fluid bottle subsystem. The pressurized air or gas also causes a fluid (e.g., a coolant or rinse liquid) within the fluid bottle subsystem to flow through the piston and out of the fluid supply subsystem where it may be used. The fluid supply system enables the fluid bottle subsystem to be installed or uninstalled from the fluid supply subsystem without requiring bleeding off of the pressurized air or gas supplied to the fluid supply system and/or without requiring the fluid bottle subsystem to be rotated or twisted into place relative to the fluid supply subsystem.

It will be appreciated that the above summary describes only some of the concepts covered in greater detail in the following detailed description. As such, claimed subject matter is not limited by the contents of this summary, and is not limited to implementations that solve any or all disadvantages noted in any part of this disclosure.

DETAILED DESCRIPTION

Figure 1:
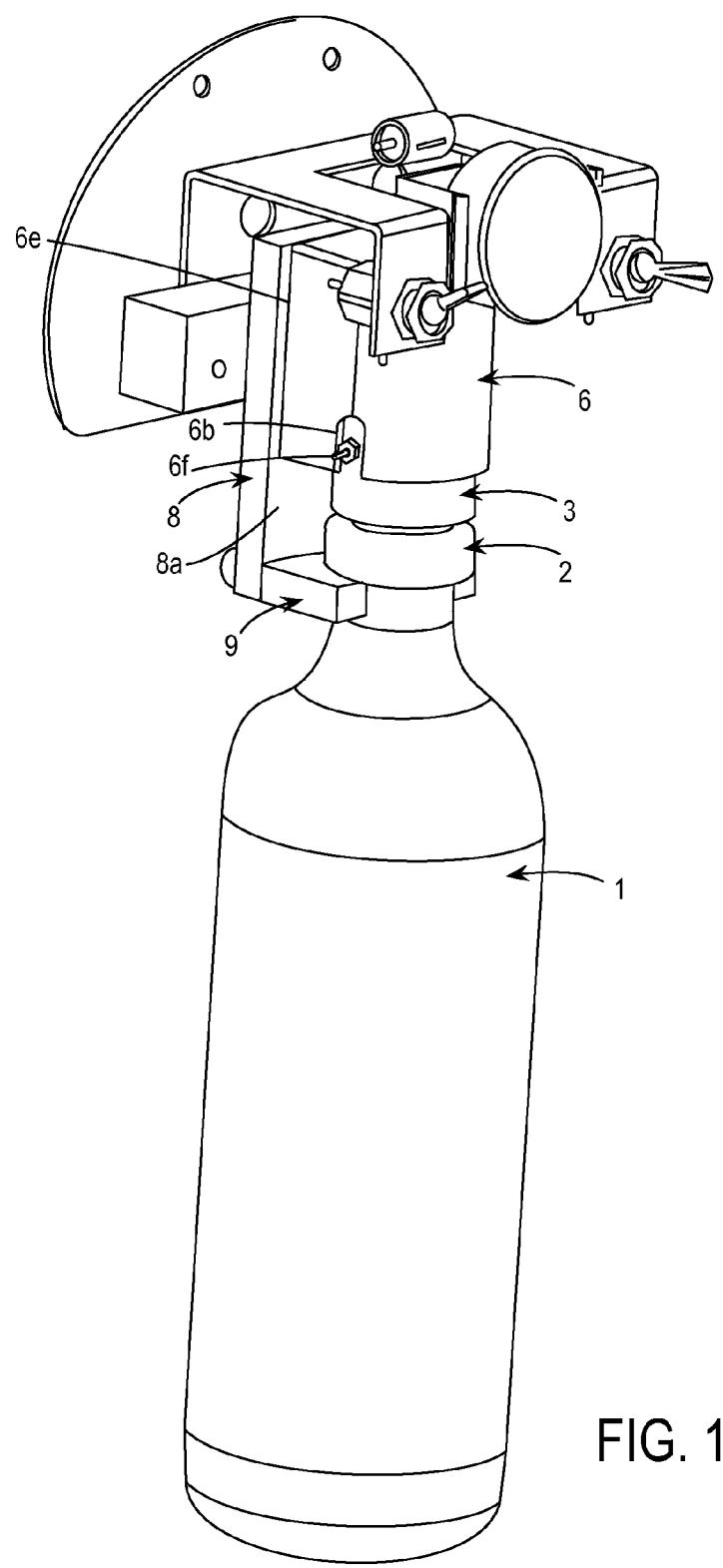
FIG. 1 is an external view of an example fluid supply system in operational delivery position.

The present disclosure pertains generally to a fluid supply system in which installation and removal of pressurized containers may be achieved without requiring the bleeding off of pressure prior to opening and/or removing a fluid bottle. In the field of dentistry, for example, it is accepted practice to rinse a patient's mouth with liquids at intervals and to use liquid coolants for the dental drills. Example liquids include tap water, distilled water, sterile water, or other suitable rinses and/or coolants. However, the disclosed concepts are not limited to a particular liquid or fluid material. In such a case, the liquid is contained in a bottle or other container adjacent to the dental chair and supplied with appropriate air pressure to provide a pressurized flow to the dental syringe and drill handpiece operated by the dentist or dental assistant.

In at least some use-scenarios, the amount of rinse and/or coolant liquid held in the fluid bottle may not be checked in light of the fluid bottle being somewhat out of the field of vision of the operator. Such a practice of providing liquids from pressurized vessels may require operators to frequently refill the bottle with the liquid, which typically requires the pressure being bled prior to opening and/or removing or installing the bottle. The use of a bleed valve and the typical requirement of screwing or unscrewing a bottle or alignment of bayonet-type quick connects often requires additional tasking and procedure on the part of the dental assistant, and is undesirable or impractical, because it often requires additional time and training, and because proper procedure may be overlooked in a busy environment.

As a non-limiting example, the present disclosure addresses some or all of these issues through use of a fluid supply system that includes a quick connect receptacle for use in combination with a piston operated seal. The piston operated seal provides a seal interface, captivation, and retention of the fluid container without necessarily requiring the depressurization of the container and/or screwing or unscrewing of the container. The fluid bottle subsystem may be connected or disconnected from the fluid supply subsystem by simply pivoting the fluid bottle subsystem in and out of the quick connect receptacle. In at least one example, the disclosed fluid supply system automatically (e.g., without a separate depressurization operation by the operator) bleeds off pressure during the removal of the container without having to turn off the air supply or unscrew or twist to unlock the container.

With attention to the drawings wherein applied numerals indicate parts/characteristics similarly hereinafter identified, FIGS. 1-4 are schematic diagrams depicting an example fluid supply system. The fluid supply system includes two primary component subsystems: (1) a fluid bottle subsystem, and (2) a fluid supply subsystem.

The fluid bottle subsystem includes a fluid bottle 1 and a collar 2. As a non-limiting example, fluid bottle 1 may take the form of a dental industry standard fluid bottle of heavy-duty construction that includes a neck having male threads 1a thereon. Collar 2 includes internal threads for engagement with bottle threads 1a, depicted in further detail in FIG. 4. Collar 2 may be removed from fluid bottle 1 by unscrewing the collar, and may be used with other fluid bottles. Hence, collar 2 may be used across a range of fluid bottles of different types or configurations. In other examples, collar 2 may be integrated with fluid bottle 1 and/or may be inseparable from fluid bottle 1. For example, the fluid bottle subsystem may take the form of an integrated fluid bottle/collar combination, which may be formed from a common material or combination of materials. While fluid bottle 1 is described as a dental industry standard fluid bottle, it will be understood that fluid bottle 1 may take the form of other fluid bottle types or configurations. Accordingly, the fluid supply system described herein is not limited to use with dental industry standard fluid bottles.

In an example configuration, the fluid supply subsystem includes one or more of a housing 6, a support 9, a mounting plate 8, a piston 3, an air supply tubing 10, a fluid pick-up tubing 11, and other components described herein. Collar 2 may include an interface surface 2a (e.g., the underside of the collar facing away from a mouth of the fluid bottle) at its distal end (e.g., perpendicular/orthogonal to an axis passing through the center of the collar). Interface surface 2a of collar 2 may be seated upon interface surface 9a, which may include the upper surface of support 9. Support 9 is affixed to housing 6 via a mounting plate 8 in this example configuration.

Figure 4:
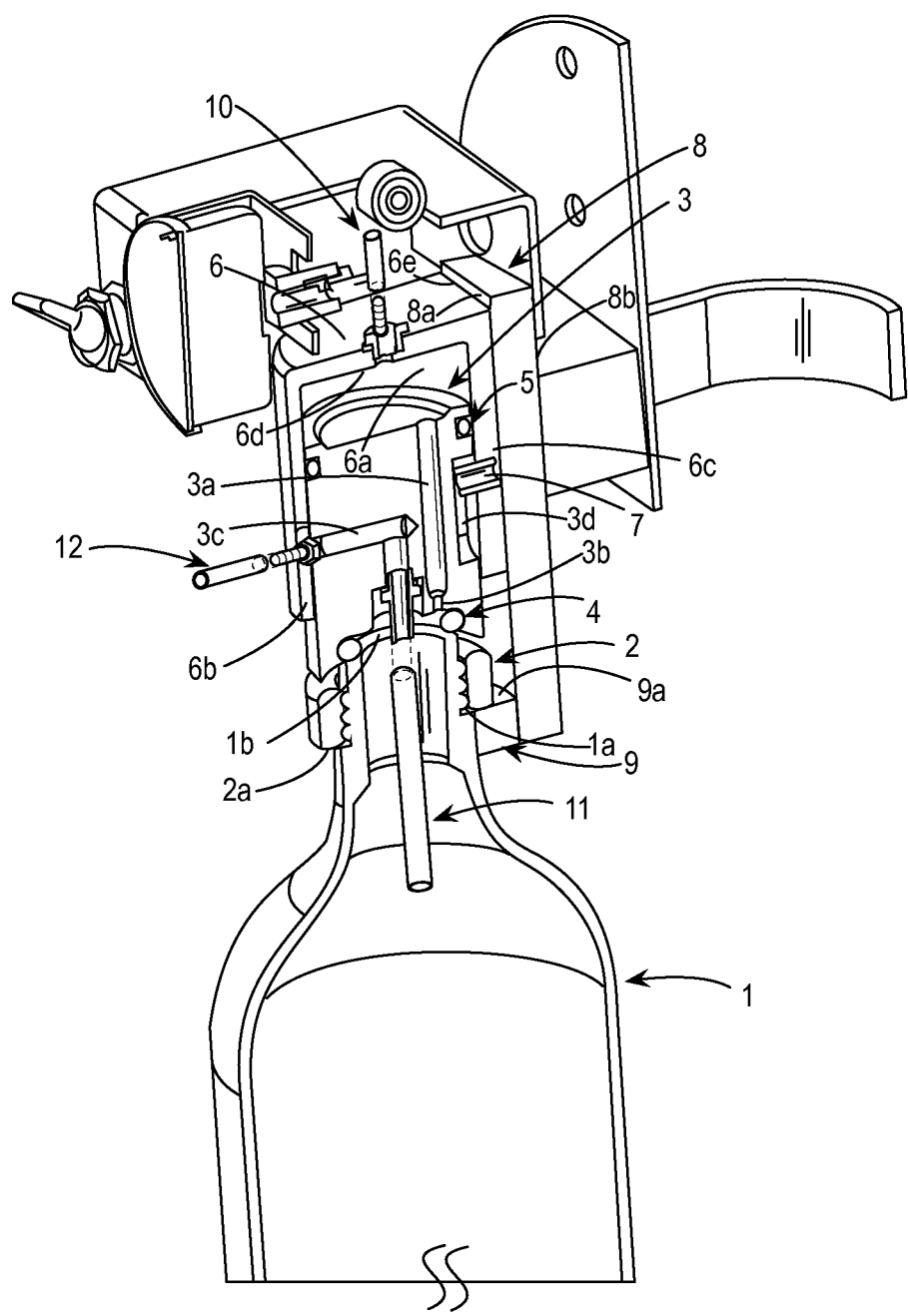
FIG. 4 is a sectional view of the fluid supply system in an operational delivery position with the fluid bottle subsystem fully captured, sealed and pressurized relative to the fluid supply subsystem.

Referring to FIG. 4, housing 6 includes or otherwise defines piston bore 6a, air inlet 6d (e.g., located at the top of the housing), fluid outlet clearance slot 6b (e.g., parallel to the axis of the piston or providing an opening sufficient for the piston to translate within housing 6), and an installation hole of pin 7 (e.g., perpendicular to the axis of the piston). In some examples, pin 7 may be integrated with and/or formed by housing 6. It will be understood that the location and orientation of the above described features of housing 6 depicted in FIG. 4 provide a non-limiting example of a housing configuration. In other configurations, one or more of these features may have different locations and/or orientations from the locations and orientations depicted in FIG. 4.

Piston 3 is located within piston bore 6a of housing 6, and is able to translate within piston bore 6a. Piston 3 includes or otherwise defines an O-ring groove at or near its proximal end to retain piston O-ring 5. Piston 5 further includes or otherwise defines an O-ring groove at its distal end to retain O-ring 4. O-ring 4 may facilitate or otherwise accommodate the sealing of fluid bottle 1 during a filling or dispensing operation between surface 1b of the fluid bottle and O-ring 4, thereby forming a seal. In another example, O-ring 4 may additionally or alternatively facilitate or otherwise accommodate the sealing of fluid bottle 1 between an upper surface of collar 2 (e.g., opposite 2a) and O-ring 4. In such case, O-ring 4 may have a larger diameter so that it is aligned with and/or contacts at least a portion of O-ring 4. Piston 5 may include additional O-rings or alternative O-ring positions from the example depicted in FIG. 4

Piston 3 includes or otherwise defines an air inlet or air exchange pathway 3a having a reduced control orifice 3b at the distal end of the piston. Orifice 3b may be omitted in some configurations. Air exchange pathway 3a enables air to pass from a first side of piston 3 containing air inlet 6d, through piston 3, out from a second side of piston 3 for delivery to bottle 1. Piston 3 includes or otherwise defines a fluid outlet port 3c. Fluid may enter the fluid outlet port 3c at the distal end of the piston (e.g., parallel to its axis or other suitable location) (e.g., via tubing 11), and may exit the fluid outlet port of the piston at a location that is perpendicular to the axis (e.g., via tubing 12 connected to nozzle 6f). It will be appreciated that the location and orientation of the features of piston 3 depicted in FIG. 4 are non-limiting examples of a piston configuration, and that these features may be located or defined by the piston at other suitable locations and/or orientations. In some examples, one or more of fluid outlet port 3c, tubing 11, and/or tubing 12 may include one or more check valves.

Piston 3 may include or otherwise define keyway 3d on an outer surface of the piston that is parallel to the axis of the piston. Keyway 3d provides upper and lower stops for pin 7 which, in this example, projects from an inner surface of the housing. Housing 6 in combination with pin 7 constrains motion of piston 3 to translation along the axis of the piston between upper and lower stops provided by keyway 3d.

Figure 2:
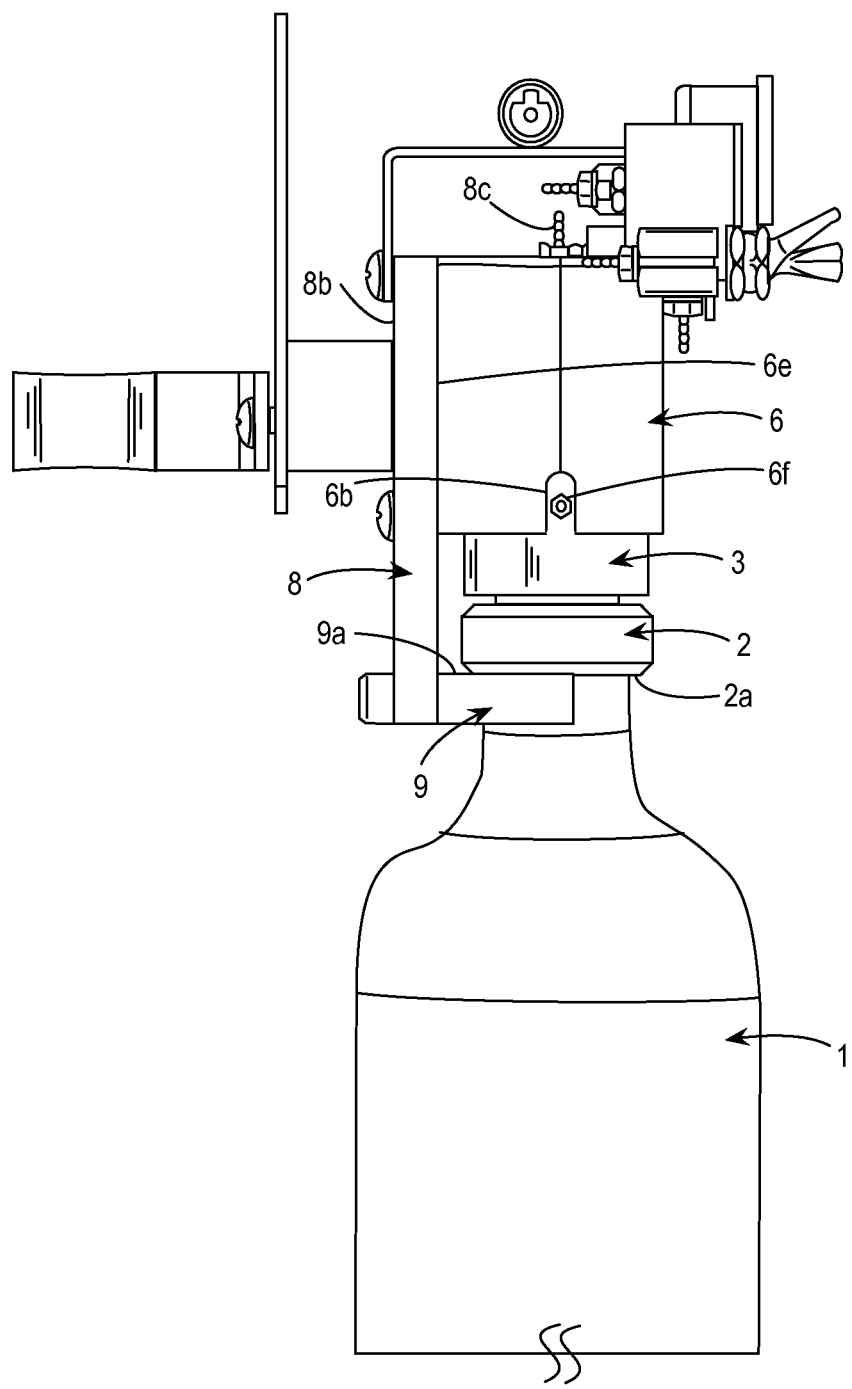
FIG. 2 is a view similar to FIG. 1 but shown in a dental unit pole mount configuration.
Figure 3:
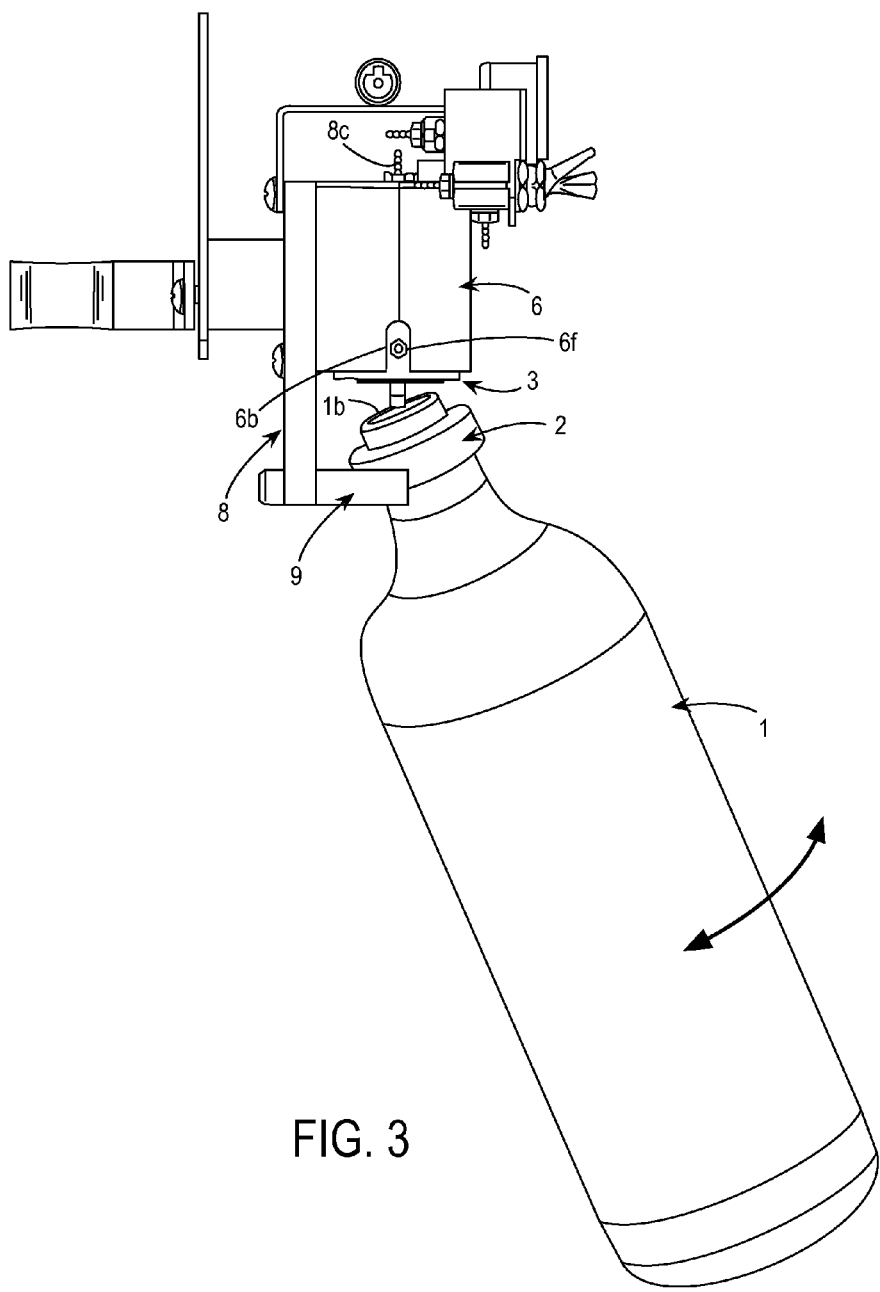
FIG. 3 is a view similar to FIG. 2 but shown in a non-operational position during fluid bottle removal or installation.

In at least some configurations, housing 6 may be mounted to a structure via a mounting plate 8. FIGS. 2 and 3 depicting non-limiting examples of the fluid supply system mounted to a structure via mounting plate 8. Housing 6 may interface with or may include (e.g., be integrated with) or otherwise define mounting plate 8. In one example, surface 6e of housing 6 interfaces with surface 8a of mounting plate 8. Surfaces 6e and 8a may be parallel to the axis of piston 3 in some examples. Mounting plate 8 may take the form of a universal mounting plate that includes mounting surface 8b that interfaces with and/or supports universal mounting bracket accessories such as dental unit post mounting, post mounted utility center mounting, cabinet mounting, or other suitable mounting configuration.

Air supply tubing 10 provides flow path communication from an air source (e.g., a pressurized gas such as air or other suitable gas) to the fluid supply system. Air (or other suitable gas) passing through air supply tubing 10 (e.g., connected to nozzle 8c) into piston bore 6a flows through air inlet 3a and reduced control orifice 3b, and into fluid bottle 1. The supply of pressurized air (or other suitable gas) to piston bore 6a further serves to translate piston 3 toward bottle 1, thereby providing a sealing force between the fluid supply subsystem and the fluid bottle subsystem.

Fluid pick-up tubing 11 provides flow path communication from fluid bottle 1 to supply tubing 12 via fluid outlet port 3c. Fluid supply tubing 12 provides flow path communication from the fluid supply system to a dental control unit or other suitable location where the fluid may be used. Fluid residing in fluid bottle 1 flows through tubing 11, fluid outlet port 3c, and tubing 12 toward the dental control unit or other suitable location.

In some configurations, the fluid supply subsystem may include fewer components and/or may include additional components. For example, the fluid supply subsystem may include housing 6, support 9, and piston 3, whereby a user of the fluid supply subsystem supplies the various tubing 10, 11, and 12, as well as a mounting structure such as mounting plate 8 for securing the fluid supply subsystem. In another example, the fluid supply subsystem includes housing 6, support 9, and piston 3, and a mounting structure such as example mounting plate 8. In still another example, the fluid supply subsystem includes housing 6, support 9, piston 3, a mounting structure such as example mounting plate 8, and one or more of the various tubing 10, 11, and 12. In at least some configurations, support 9 may be integrated with housing 6 via a mounting structure, such as example mounting plate 8 or other suitable support arm.

In at least some examples, the fluid bottle subsystem and the fluid supply subsystem may form a quick connect interface that does not require twisting or threading to connect or remove fluid bottles. The fluid bottle subsystem may be installed and/or removed from the fluid supply subsystem even while air pressure is supplied to the fluid supply system via air supply tubing 10. In an example use-scenario, an operator may pivot the fluid bottle subsystem in or out of its operating position as shown in FIG. 3.

It should be understood that the disclosed embodiments are illustrative and not restrictive. Variations to the disclosed embodiments that fall within the metes and bounds of the claims, now or later presented, or equivalence of such metes and bounds are intended to be embraced by the claims. While the example embodiments of a fluid supply system have been described herein, it will be apparent to those skilled in the art that aspects of the fluid supply system may be embodied in other forms without departing from the spirit and scope of the disclosed subject matter. Such embodiments may include but are not limited to air on-off switches, water source (city or bottled) selector switches, air regulators, air pressure gauges, fluid filters, etc.

The invention claimed is:

1. A fluid supply system, comprising:
   a housing defining a piston bore and an air inlet passing through the housing at a first end of the piston bore;
   a piston housed and translatable within the piston bore, the piston defining a fluid outlet path through at least a portion of the piston and an air inlet path through at least a portion of the piston, a first end of the fluid outlet path and a first end of the air inlet path defined in a proximal end of the piston opposite a distal end of the piston, the distal end of the piston nearest the first end of the piston bore; and
   an O-ring located at the proximal end of the piston to interface with a mouth of a fluid bottle.

2. The fluid supply system of claim 1, wherein the O-ring seals the mouth of fluid bottle to the proximal end of the piston; and
   wherein the first end of the fluid outlet path and the first end of the air inlet path are defined in a region of the proximal end of the piston surrounded by the O-ring.

3. The fluid supply system of claim 2, wherein a second end of the fluid outlet path is defined in a side of the piston.

4. The fluid supply system of claim 3, wherein the housing further defines an opening in a side of the piston bore, the opening aligned with the second end of the fluid outlet path defined in the side of the piston.

5. The fluid supply system of claim 4, wherein the opening defined in the side of the piston bore is a slot that is parallel to an axis of translation of the piston within the piston bore.

6. The fluid supply system of claim 5, further comprising:
   a nozzle connected to the second end of the fluid outlet path, the nozzle projecting through the opening defined in the side of the piston bore.

7. The fluid supply system of claim 6, further comprising:
   fluid supply tubing communicating with the second end of the fluid outlet path and providing a flow path for fluid from the fluid supply system via the nozzle.

8. The fluid supply system of claim 1, wherein the second end of the air inlet path is defined in the distal end of the piston.

9. The fluid supply system of 8, wherein the air inlet path includes a reduced orifice defined by the piston along a portion of the air inlet path.

10. The fluid supply system of 9, wherein the reduced orifice is located at the first end of the air inlet path.

11. The fluid supply system of claim 1, further comprising:
    a nozzle external the housing and connected to the air inlet that passes through the housing.

12. The fluid supply system of claim 11, further comprising:
    an air supply tubing communicating with the air inlet and providing a flow path for air to the nozzle.

13. The fluid supply system of claim 1, wherein the housing further defines or includes a pin that projects inward from the housing into the piston bore; and
    wherein the piston defines a keyway that is parallel to an axis of translation of the piston within the piston bore, and provides upper and lower stops at opposite ends of the keyway to constrain the pin projecting into the keyway between the upper and lower stops.

14. The fluid supply system of claim 1, further comprising a support affixed to or integrated with the housing, the support including a first interface surface that faces toward the proximal end of the piston, the first interface surface interfacing with a second interface surface of a fluid bottle subsystem that includes the fluid bottle while the O-ring interfaces with the mouth of the fluid bottle.

15. The fluid supply system of claim 14, further comprising:
    a collar having threads for receiving corresponding threads of the fluid bottle, the collar including the second interface surface interfacing with the first interface surface of the support.

16. The fluid supply system of claim 15, wherein the second interface surface faces away from an opening defined by the mouth of the fluid bottle while the collar is threaded onto the fluid bottle and while the O-ring interfaces with the mouth of the fluid bottle.

17. The fluid supply system of claim 15, further comprising the fluid bottle subsystem including the fluid bottle and the collar.

18. A fluid supply system, comprising:
    a fluid bottle subsystem that includes:
       a fluid bottle, and
       a collar surrounding a neck of the fluid bottle; and
    a fluid supply subsystem that includes:
       a housing defining a piston bore and an air inlet passing through the housing at a first end of the piston bore,
       a piston housed and translatable within the piston bore, the piston defining a fluid outlet path through at least a portion of the piston and an air inlet path through at least a portion of the piston, a first end of the fluid outlet path and a first end of the air inlet path defined in a proximal end of the piston opposite a distal end of the piston, the distal end of the piston nearest the first end of the piston bore,
       an O-ring located at the proximal end of the piston to interface with a mouth of a fluid bottle in which the O-ring seals the mouth of fluid bottle to the proximal end of the piston such that the first end of the fluid outlet path and the first end of the air inlet path are defined in a region of the proximal end of the piston surrounded by the O-ring, and
       a support affixed to or integrated with the housing, the support including a first interface surface that faces toward the proximal end of the piston, the first interface surface interfacing with a second interface surface of the collar while the O-ring interfaces with the mouth of the fluid bottle, the second interface surface facing away from an opening defined by the mouth of the fluid bottle while the collar is threaded onto the fluid bottle and while the O-ring interfaces with the mouth of the fluid bottle.

19. The fluid supply system of claim 18, wherein a second end of the fluid outlet path is defined in a side of the piston;
    wherein the housing further defines an opening in a side of the piston bore, the opening aligned with the second end of the fluid outlet path defined in the side of the piston;
    wherein the second end of the air inlet path is defined in the distal end of the piston; and
    wherein the air inlet path includes a reduced orifice defined by the piston at the first end of the air inlet path.

20. The fluid supply system of claim 18, wherein the collar is integrated with the fluid bottle.

* * * * *